(12) United States Patent
Ino

(10) Patent No.: US 9,325,430 B2
(45) Date of Patent: Apr. 26, 2016

(54) COMMUNICATION SYSTEM AND COMMUNICATION APPARATUS

(75) Inventor: Hiroyuki Ino, Tokyo (JP)

(73) Assignee: SONY CORPORATION, Tokyo (JP)

( * ) Notice: Subject to any disclaimer, the term of this patent is extended or adjusted under 35 U.S.C. 154(b) by 385 days.

(21) Appl. No.: 13/177,750

(22) Filed: Jul. 7, 2011

(65) Prior Publication Data

US 2012/0013446 A1  Jan. 19, 2012

(30) Foreign Application Priority Data

Jul. 14, 2010 (JP) ................ P2010-159986

(51) Int. Cl.
| | |
|---|---|
| *H04B 13/00* | (2006.01) |
| *G06K 19/07* | (2006.01) |
| *G06K 19/067* | (2006.01) |
| *A61B 5/00* | (2006.01) |
| *A61B 5/024* | (2006.01) |
| *A61B 5/0245* | (2006.01) |

(52) U.S. Cl.
CPC ............ *H04B 13/005* (2013.01); *A61B 5/0024* (2013.01); *A61B 5/0028* (2013.01); *A61B 5/0245* (2013.01); *A61B 5/02438* (2013.01); *G06K 19/0672* (2013.01); *G06K 19/0724* (2013.01); *G06K 19/0726* (2013.01); *A61B 2560/0209* (2013.01); *A61B 2560/0214* (2013.01)

(58) Field of Classification Search
CPC ....... G06K 7/00; G06K 7/0008; G06K 19/07; G06K 19/067; G06K 19/0672; G06K 19/0701; G06K 19/0716; G06K 19/0723–19/0726; H04B 13/005

USPC ................. 340/10.1–10.52, 572.1–572.9
See application file for complete search history.

(56) References Cited

U.S. PATENT DOCUMENTS

| | | | | |
|---|---|---|---|---|
| 5,201,060 | A | * | 4/1993 | Haruyama et al. .............. 455/45 |
| 5,434,572 | A | | 7/1995 | Smith |
| 5,455,575 | A | * | 10/1995 | Schuermann ................... 342/42 |
| 6,731,199 | B1 | * | 5/2004 | Ueda ............................ 340/10.4 |
| 6,850,583 | B1 | * | 2/2005 | Matsumura et al. .......... 375/376 |
| 8,180,288 | B2 | * | 5/2012 | Hebiguchi et al. ........... 455/41.1 |
| 2001/0001758 | A1 | * | 5/2001 | Greeff et al. .................... 455/41 |
| 2003/0095033 | A1 | * | 5/2003 | Amtmann .................... 340/10.1 |
| 2005/0052286 | A1 | * | 3/2005 | Perraud et al. ........... 340/825.72 |
| 2005/0104790 | A1 | * | 5/2005 | Duron ........................... 343/745 |
| 2005/0135514 | A1 | * | 6/2005 | Suzuki et al. ................. 375/345 |

(Continued)

FOREIGN PATENT DOCUMENTS

| | | |
|---|---|---|
| JP | 63-005286 A | 1/1988 |
| JP | 01-314985 A | 12/1989 |

(Continued)

OTHER PUBLICATIONS

Marc Simon Wegmüller, "Intra-Body Communication for Biomedical Sensor Networks", 2007, Chapter 1 and 6.*

*Primary Examiner* — Amine Benlagsir
*Assistant Examiner* — Orlando Bousono
(74) *Attorney, Agent, or Firm* — Hazuki International, LLC

(57) ABSTRACT

A communication system includes: an interrogator transmitting an interrogation signal while switching a carrier-wave frequency and receiving a response signal; and a plurality of responders each having a unique resonant frequency and returning the response signal in response to the interrogation signal with the own resonant frequency.

11 Claims, 3 Drawing Sheets

(56) References Cited

U.S. PATENT DOCUMENTS

| | | | |
|---|---|---|---|
| 2005/0253747 A1* | 11/2005 | Taki et al. | 342/42 |
| 2006/0113397 A1* | 6/2006 | Beilenhoff et al. | 235/494 |
| 2006/0171496 A1* | 8/2006 | Nakamuta et al. | 375/376 |
| 2007/0018792 A1* | 1/2007 | Taki et al. | 340/10.1 |
| 2007/0096881 A1* | 5/2007 | Pillai | 340/10.51 |
| 2008/0012710 A1* | 1/2008 | Sadr | 340/572.1 |
| 2008/0079548 A1* | 4/2008 | Hayama et al. | 340/10.4 |
| 2008/0231332 A1* | 9/2008 | Nakata et al. | 327/147 |
| 2008/0266059 A1* | 10/2008 | Murofushi et al. | 340/10.3 |
| 2009/0251288 A1* | 10/2009 | Nikitin et al. | 340/10.1 |
| 2009/0303004 A1* | 12/2009 | Tuttle | 340/10.1 |
| 2009/0304135 A1* | 12/2009 | Suzuki et al. | 375/354 |
| 2010/0019982 A1* | 1/2010 | Washiro | 343/860 |
| 2010/0049279 A1* | 2/2010 | Seeberger et al. | 607/59 |
| 2010/0109844 A1* | 5/2010 | Carrick et al. | 340/10.1 |
| 2011/0133895 A1* | 6/2011 | Wu et al. | 340/10.1 |

FOREIGN PATENT DOCUMENTS

| | | |
|---|---|---|
| JP | 6-201821 A | 7/1994 |
| JP | 2000-131423 A | 5/2000 |

\* cited by examiner

COMMUNICATION SYSTEM AND COMMUNICATION APPARATUS

CROSS-REFERENCE TO RELATED APPLICATION

The present application claims priority from Japanese Patent Application No. JP 2010-159986 filed in the Japanese Patent Office on Jul. 14, 2010, the entire content of which is incorporated herein by reference.

BACKGROUND

The present disclosure relates to a communication system and a communication apparatus which includes an interrogator transmitting an interrogation signal and responders returning a response signal in response to the interrogation signal, and more particularly, to a communication system and a communication apparatus which includes one interrogator and a plurality of responders and in which the interrogator sequentially communicates with the respective responders while preventing a collision error.

A communication system such as RFID includes an interrogator transmitting an interrogation signal and a responder returning a response signal in response to the interrogation signal. Many kinds of communication systems perform non-contact communication or proximity communication. The responder has the features of low power consumption and low cost to obtain driving power from the interrogation signal. In general, since the communication system includes one interrogator and a plurality of responders, it is desirable that the interrogator efficiently communicates with the plurality of responders.

For example, when a unique identification code and a random code having a hierarchical structure are written into an IC tag and no search can be performed due to collision of the random code of Layer zero, the search is performed with the random code of Layer one. There has been suggested a communication method of accelerating search of an IC card by performing search in each layer (for example, see Japanese Unexamined Patent Application Publication No. 2000-131423).

Moreover, there has been suggested a system in which a responder changes a transmission timing at random, returns an operation response signal, stores identification codes included in the operation response signal received by an interrogator in a predetermined sequence, stops communication for a predetermined period when communication normally ends, correctly recognizes all of the plurality of unspecified responders, and reduces a probability that the operation response signals of the responders collide with each other (for example, see Japanese Unexamined Patent Application Publication No. 6-201821).

Furthermore, there has been suggested a communication method in which the unique identification codes of the respective responders are stored, an interrogator transmits a data request signal attached with the identification code of a responder with which the interrogator desires to communicate, and only the responder having the own identification code matching with the identification code responds to the data request signal (for example, Japanese Unexamined Patent Application Publication No. 63-5286, Japanese Unexamined Patent Application Publication No. 1-314985, and U.S. Pat. No. 5,434,572).

In a communication system including one interrogator and a plurality of responders, there is a concern that a collision error occurs when the interrogator simultaneously receives responses from the plurality of responders. When the collision error occurs, the interrogator has to transmit the interrogation signal again and give a request for supplying information to the responders. However, a problem may arise in that communication efficiency may deteriorate and the interrogator may not acquire necessary information from the responders.

Moreover, the responders have to be in a standby state to respond to the interrogation signal from the interrogator. The responders consume power when the responders are in the standby state. Therefore, the responders may become a cause of heat generation or a noise source for the other responders. When the responder is equipped with a measurement mechanism such as a temperature sensor, correct sensor information may not be acquired due to the heat or noise generated from the responder.

When the interrogator is configured to transmit an interrogation signal designated for an individual responder, the collision error may be prevented. In this case, however, the responder has to include the function of a reception circuit to understand an interrogation from the interrogator (perform decoding). For this reason, the size of the responder may be increased, and thus an increase in power consumption and high cost may be caused.

SUMMARY

It is desirable to provide a communication system and a communication apparatus that include one interrogator and a plurality of responders and that are excellent in preventing a collision error from occurring when the interrogator simultaneously receives responses from the plurality of responders.

According to an embodiment of the disclosure, there is provided a communication system including an interrogator transmitting an interrogation signal while switching a carrier-wave frequency and receiving a response signal; and a plurality of responders each having a unique resonant frequency and returning the response signal in response to the interrogation signal with the own resonant frequency.

The "system" described herein refers to a system in which a plurality of apparatuses (or functional modules realizing a specific function) are logically assembled. The respective apparatuses or functional modules may or may not be disposed in a single case.

In the communication system according to the embodiment of the disclosure, the interrogator may transmit the interrogation signal from a power feeding electrode to a human body serving as a communication medium and receive the response signal via the human body using the power feeding electrode. The plurality of responders may each include a sensor acquiring biological information from the human body, receive the interrogation signal with the own resonant frequency transmitted via the human body using a power reception electrode, and transmit the response signal, in which the biological information acquired by the sensor is superimposed, from the power reception electrode to the human body.

According to another embodiment of the disclosure, there is provided a communication apparatus including: an oscillation unit switching an oscillation frequency; a transceiver transmitting an interrogation signal with a frequency oscillated in the oscillation unit to a communication medium and receiving a response signal from the communication medium; and a demodulation unit demodulating the received response signal. The interrogation signal is transmitted and the response signal is received, while the frequency oscillated in the oscillation unit is changed.

In the communication apparatus according to the embodiment of the disclosure, the transceiver may be configured by a power feeding electrode being in contact with a human body serving as the communication medium.

According to still another embodiment of the disclosure, there is provided a communication apparatus including: a transceiver transmitting and receiving a signal via a communication medium; a power reception unit resonating by an interrogation signal with a unique frequency; and a transmission unit generating a response signal, in which transmission information is superimposed, in response to the received interrogation signal.

In the communication apparatus according to the embodiment of the disclosure, the transceiver may be configured by a power reception electrode being in contact with a human body serving as the communication medium.

In the communication apparatus according to the embodiment of the disclosure, the power reception unit may resonate by the interrogation signal with the unique frequency, generate constant-voltage power, and operate the transmission unit to transmit the response signal when the constant-voltage power has a reception voltage sufficient to drive at least a part of the circuits.

In the communication apparatus according to the embodiment of the disclosure, the transceiver may be configured by a power reception electrode being in contact with a human body serving as the communication medium. The communication apparatus may further include a sensor function unit acquiring biological information from the human body. The transmission unit may generate the response signal, in which transmission information is superimposed, in response to the received interrogation signal.

In the communication apparatus according to the embodiment of the disclosure, the transmission unit may transmit the response signal subjected to load modulation based on the transmission information from the transceiver in response to the interrogation signal formed of non-modulated carrier waves of the unique frequency.

In the communication apparatus according to the embodiment of the disclosure, the power reception unit may include a clock generation circuit generating a clock necessary for a digital operation of the transmission unit or another circuit from the interrogation signal formed of the unique carrier waves.

According to the embodiments of the disclosure, it is possible to provide the communication system and the communication apparatus that include one interrogator and the plurality of responders and are excellent in preventing a collision error from occurring when the interrogator simultaneously receives responses from the plurality of responders.

According to the embodiments of the disclosure, a unique resonant frequency is allocated to a power reception circuit of each of the responders. Therefore, by transmitting an interrogation signal with a unique oscillation frequency of the responder to which the interrogator desires to interrogate, the interrogation signal can be fed only to the specific responder tuned to the oscillation frequency, the response signal can be received, and thus information can be obtained. Since the interrogator can sequentially acquire information from the plurality of responses one by one by appropriately switching the oscillation frequency, it is possible to prevent communication efficient from deteriorating due to a collision error.

According to the embodiment of the disclosure, the responders each autonomously operate a transmission circuit and transmit the response signal, when a received voltage reaches a predetermined value. Only when each responder receives the interrogation signal with the unique oscillation frequency to which the power reception circuit is tuned, each responder operates the transmission circuit. Therefore, since the responders may not normally be in the standby state, it is possible to prevent unnecessary noise occurrence, heat generation, and power consumption.

According to the embodiments of the disclosure, each responder operates the transmission circuit, only when each responder receives the interrogation signal with the unique oscillation frequency. In other words, since it is not necessary to provide the function of the reception circuit to understand the interrogation from the interrogator (perform decoding), a small-sized apparatus can be maintained, thereby realizing low power consumption and low cost.

According to the embodiments of the disclosure, communication of a human body is applicable to the communication system according to the embodiment of the disclosure. In this case, when the plurality of responders are disposed on the respective parts of the human body so that the respective power reception electrodes come into contact with the human body, the interrogator can acquire the response signals from the respective responders from the power feeding electrodes coming into contact with the human body. For example, when each responder has the sensor function of acquiring biological information, the interrogator can acquire the biological information of the respective parts of the human body from the respective responders and prevent a collision error, by transmitting the interrogation signal while switching the oscillation frequency. Moreover, only when each responder receives the interrogation signal with the unique oscillation frequency, each responder operates the transmission circuit. Therefore, since unnecessary noise does not occur during a period other than the period in which the transmission circuit is operated, the biological signal can be acquired from a weak sensor signal without receiving an influence of the noise from the other responders.

The other objects, features, and advantages of the embodiments of the disclosure will be apparent from the detailed description based on the embodiments and accompanying drawings described below.

DETAILED DESCRIPTION OF EMBODIMENTS

Hereinafter, an embodiment of the disclosure will be described in detail with reference to the drawings.

Figure 1:
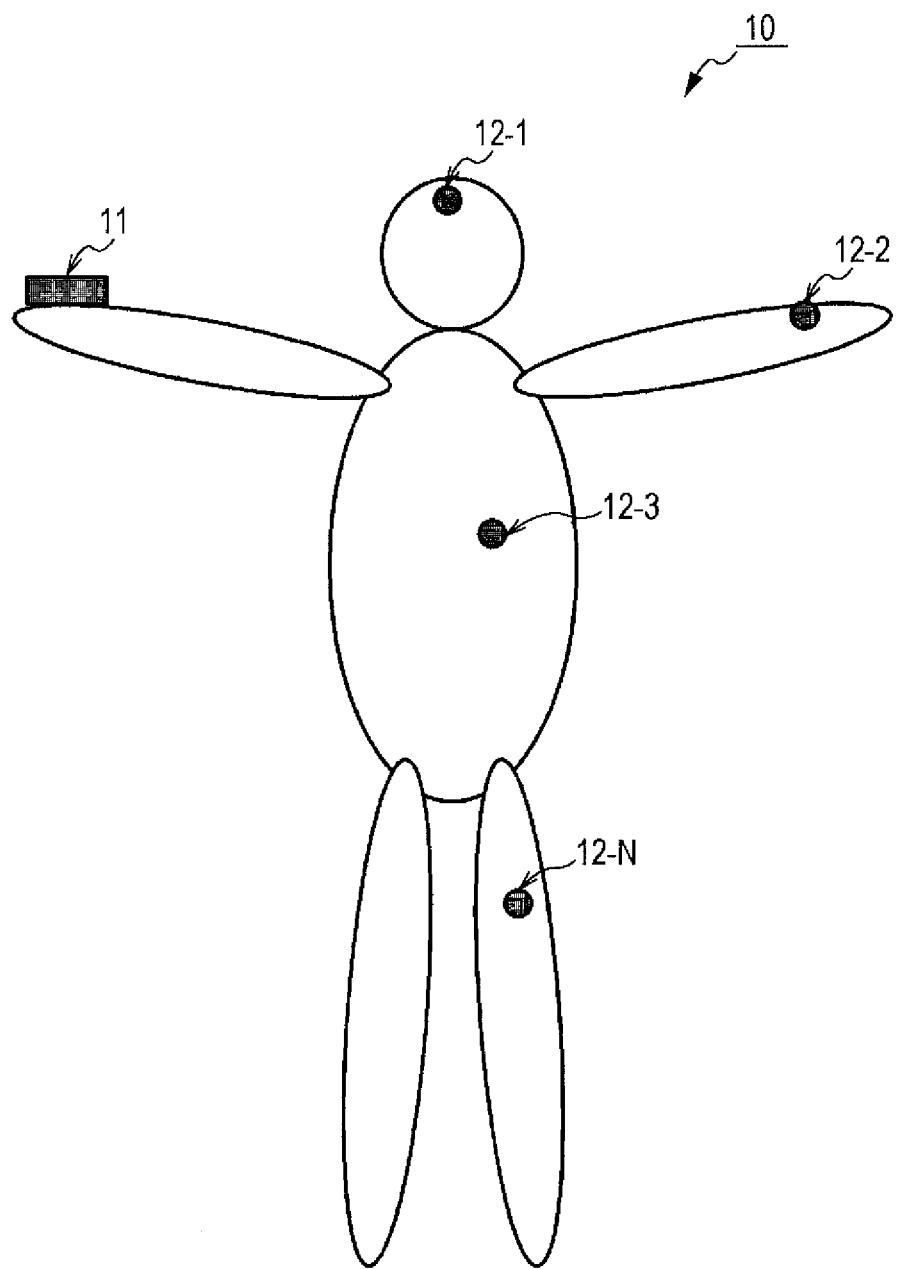
FIG. 1 is a diagram schematically illustrating an example of the configuration of a communication system according to an embodiment of the disclosure.

FIG. 1 is a diagram schematically illustrating an example of the configuration of a communication system according to an embodiment of the disclosure. Communication of a human body is applied to a communication system 10 illustrated in the drawing. A plurality of responders 12-1, 12-2, and so on, is disposed on respective parts of a human body and an interrogator 11 is held, for example, on the palm of his or her hand. The responders 12-1, 12-2, and so on, have basically the same configuration. However, according to the gist of the disclosure, the interrogator 11 and the responders 12-1, 12-2, and so on, may not be disposed at specific positions.

A unique resonant frequency can be allocated to a power reception circuit of each of the responders 12-1, 12-2, and so on. In addition, the interrogator 11 transmits a response signal with a unique oscillation frequency to each of the responders 12-1, 12-2, and so on, to which the interrogator 11 desires to interrogate, using the human body as a medium. As a result, power is fed only to one responder tuned to the oscillation frequency among the responders 12-1, 12-2, and so on. When a received voltage reaches a predetermined value, the responders 12-1, 12-2, and so on, each autonomously operates a transmission circuit and transmit a response signal using the human body as a medium. Accordingly, the interrogator 11 switches the oscillation frequency and transmits an interrogation signal to acquire information sequentially from the plurality of responders 12-1, 12-2, and so on, one by one, thereby preventing communication efficiency from deteriorating due to a collision error.

The responders 12-1, 12-2, and so on, each operate the transmission circuit only when receiving the interrogation signal with the unique oscillation frequency to which the power reception circuit is tuned. Therefore, it is not necessary for the responders to be normally in a standby state. Accordingly, the responders 12-1, 12-2, and so on, can each prevent unnecessary heat generation or power consumption. When the other responder operates the transmission circuit, the responder itself does not operate the transmission circuit. Therefore, the responders 12-1, 12-2, and so on, do not become an unnecessary noise generation source for one another. The responders 12-1, 12-2, and so on, operate the transmission circuit and return the response signal to the interrogator 11, only when receiving the interrogation signal with the unique oscillation frequency. Moreover, it is not necessary to provide the function of the reception circuit to understand an interrogation from the interrogator 11 (perform a decoding process). Therefore, since a small-sized apparatus can be maintained, it is possible to realize low power consumption and low cost.

In the communication system 10 shown in FIG. 1, the responders 12-1, 12-2, and so on, each have a sensor function of acquiring biological information and thus are configured to transmit the response signal having the biological information. The sensor function is configured to acquire, for example, a heart rate of the human body as the biological information. Accordingly, the interrogator 11 can acquire the biological information regarding each part of the human body from the respective responders, while preventing a collision error by switching the oscillation frequency and transmitting the interrogation signal.

Here, the responders 12-1, 12-2, and so on, each include a sensor electrode configured to acquire the biological information from a weak sensor signal. The responders 12-1, 12-2, and so on, each operate the transmission circuit, only when receiving the interrogation signal with the unique oscillation frequency. In other words, when the other responders operate the transmission circuit, the responder itself does not operate the transmission circuit. In addition, unnecessary noise does not occur during other period in which the responders 12-1, 12-2, and so on, do not become a noise generation source unnecessary for one another. Therefore, each responder can acquire the biological signal from a weak sensor signal without receiving an influence of the noise from the other responders.

Figure 2:
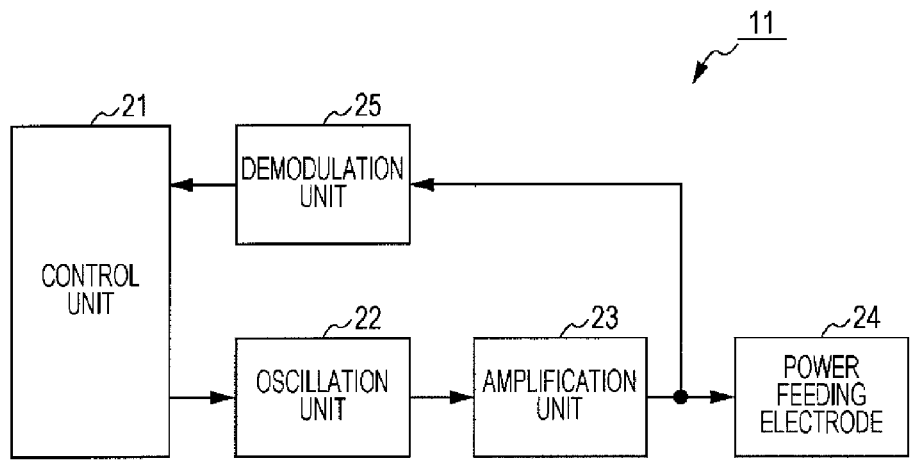
FIG. 2 is a diagram schematically illustrating an example of the configuration of an interrogator.

FIG. 2 is a diagram schematically illustrating an example of the configuration of the interrogator 11. The illustrated interrogator 11 includes a control unit 21, an oscillation unit 22, an amplification unit 23, a power feeding electrode 24, and a demodulation unit 25.

The control unit 21 not only exchanges information with an external device, such as each of the responders 12-1, 12-2, and so on, other than the interrogator 11, but also controls all of the operations of the interrogator 11.

The oscillation unit 22 has a function of switching the oscillation frequency and generates an alternating-current signal with a specific frequency based on an instruction from the control unit 21. Here, the specific frequency is a resonant frequency to which the reception circuit of each of the responders 12-1, 12-2, and so on, is tuned.

The alternating-current signal output from the oscillation unit 22 is appropriately amplified by the amplification unit 23, and then is supplied to the power feeding electrode 24. Since the power feeding electrode 24 is in contact with the human body such as the palms serving as a communication medium, the supplied alternating-current signal is transmitted as an interrogation signal formed by non-modulated carrier waves to the human body and reaches each of the responders 12-1, 12-2, and so on.

Several responders 12-1, 12-2, and so on, having the reception circuit tuned to the frequency of the non-modulated carrier waves transmitted by the interrogator 11 generate power from the non-modulated carrier waves. Moreover, when these devices operate the transmission circuit using this power, the transmission circuits generate a response signal in which information (for example, biological information such as a heart rate) is superimposed on the non-modulated carrier waves and transmit the response signal using the human body as a medium.

When the power feeding electrode 24 of the interrogator 11 receives the response signals, the demodulation unit 25 extracts the information superimposed in the response signal. When the control unit 21 determines that the information such as biological information is completely acquired from one responder, the control unit 21 instructs the oscillation unit 22 to perform conversion of the oscillation frequency in order to acquire the information from the other responders. The interrogation signals formed of the non-modulated carrier waves of other frequencies are sequentially transmitted from the power feeding electrode 24 using the human body as a medium.

Figure 3:
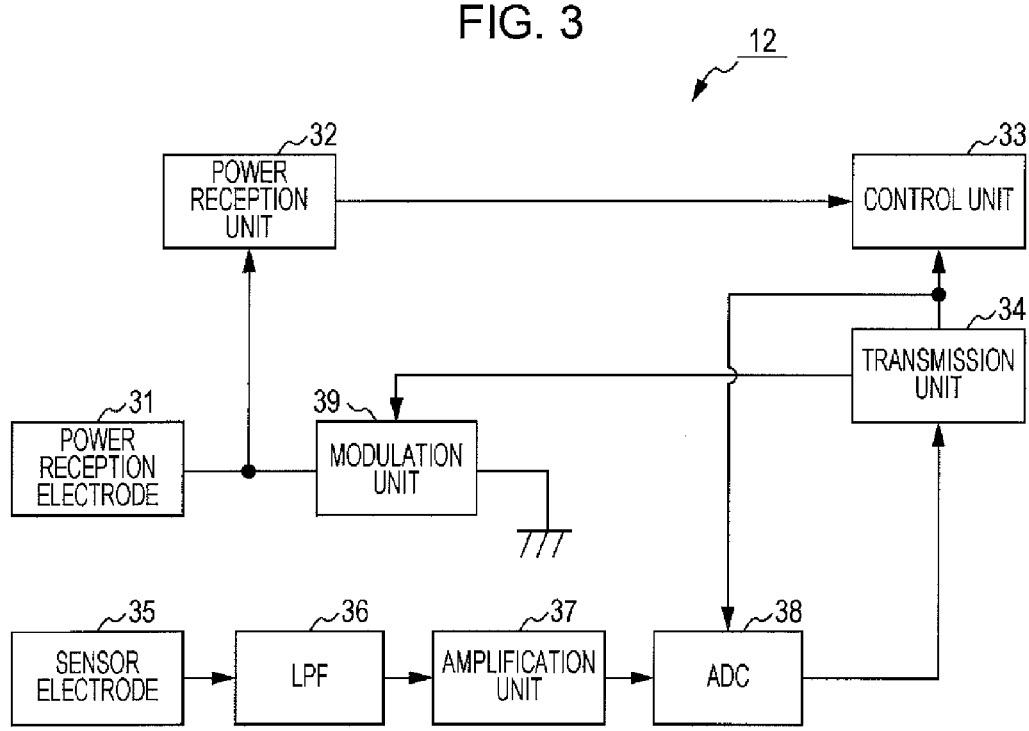
FIG. 3 is a diagram schematically illustrating an example of the configuration of a responder.

FIG. 3 is a diagram schematically illustrating an example of the configuration of the responder 12. The illustrated responder 12 has a sensor function to acquire the biological information. In the communication system shown in FIG. 1, the responders 12-1, 12-2, and so on, disposed on the parts of the human body have basically the same configuration, except that each responder can allocate the unique resonant frequency to the reception circuit.

The illustrated responder 12 includes a power reception electrode 31, a power reception unit 32, a control unit 33, a transmission unit 34, a sensor electrode 35, a low-band pass filter (LPF) 36, an amplification unit 37, an analog/digital conversion circuit (ADC) 38, and a modulation unit 39.

Since the power reception electrode 31 is in contact with a predetermined part of the human body serving as a communication medium, the power reception electrode 31 can receive the non-modulated carrier waves with a specific frequency transmitted from the interrogator 11 using the human body as a medium.

The power reception unit 32 includes a resonant circuit (which is not shown in FIG. 3) resonating at a frequency unique for the responder 12 with respect to the signal received by the power reception electrode 31, generates power of a constant voltage from the output of the resonant circuit, detects whether the constant voltage is a reception voltage sufficient to drive the responder 12, and outputs a power detection signal. Only when receiving a specific frequency, the responder 12 can return a response signal. Therefore, the non-modulated carrier waves of the specific frequency have the role of an interrogation signal.

The control unit 33 controls all of the operations of the responder 12. When the control unit 33 receives the power detection signal from the power reception unit 32, the control unit 33 gives instructions to acquire the biological information and transmit the response signal in which the acquired biological information is superimposed.

Since the sensor electrode 35 is in contact with a predetermined part of the human body, the sensor electrode 35 detects a heart rate or the like and outputs a sensor signal. The low-band pass filter 36 extracts the component of the necessary band (removes the unnecessary component) from the sensor signal, the amplification unit 37 appropriately amplifies the sensor signal, and the ADC 38 samples and quantizes the sensor signal to generate digital biological information.

When the transmission unit 34 receives the instruction to transmit the response signal from the control unit 33, the transmission unit 34 digitally modulates the biological information acquired from the ADC 38 in accordance with a predetermined format. The modulation unit 39 modulates the non-modulated carrier waves received by the power reception electrode 31 based on the transmission information subjected to the digital modulation. The modulated carrier waves are transmitted as the response signal from the power reception electrode 31 to the human body serving as a communication medium.

In the example shown in FIG. 3, the modulation unit 39 switches the state of the terminal of the power reception electrode 31 to the open or ground state and changes a load. This modulation method is one of the modulation methods used in a passive communication and is also called load modulation. Since it is not necessary for the responder 12 itself to send the carrier waves, the device can be configured to be miniaturized, be inexpensive, and consume low power.

Figure 4:
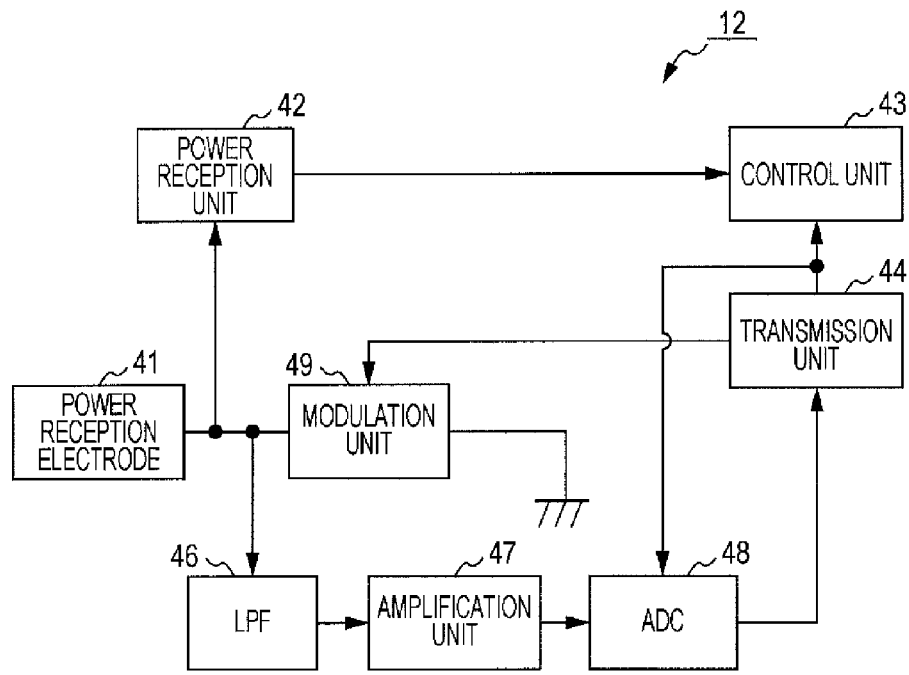
FIG. 4 is a diagram illustrating the responder shown in FIG. 3 according to a modified example.

FIG. 4 is a diagram illustrating the responder 12 shown in FIG. 3 according to a modified example. The illustrated responder 12 includes a power reception electrode 41, a power reception unit 42, a control unit 43, a transmission unit 44, a low-band pass filter (LPF) 46, an amplification unit 47, an analog/digital conversion circuit (ADC) 48, and a modulation unit 49. The power reception electrode 41 has a configuration different from the configuration shown in FIG. 3 in that the power reception electrode 41 also serves as a sensor electrode.

Since the power reception electrode 41 is in contact with a predetermined part of the human body serving as a communication medium, the power reception electrode 41 receives the non-modulated carrier waves from the interrogator 11 using the human body as a medium.

The power reception unit 42 includes a resonant circuit (which is not shown in FIG. 4) resonating at a frequency unique for the responder 12 and the resonant circuit resonates in the received signal having a unique frequency and generates power of a constant voltage. When the power reception unit 42 obtains a sufficient reception voltage, the power reception unit 42 outputs a power detection signal.

The power reception electrode 41 detects a heart rate or the like and outputs a sensor signal. The low-band pass filter 46 extracts the component of the necessary band (removes the unnecessary component) from the sensor signal, the amplification unit 47 appropriately amplifies the sensor signal, and the ADC 48 samples and quantizes the sensor signal to generate digital biological information.

When the transmission unit 44 receives the instruction to transmit the response signal from the control unit 43, the transmission unit 44 digitally modulates the biological information acquired from the ADC 48 in accordance with a predetermined format. The modulation unit 49 performs load modulation on the non-modulated carrier waves received by the power reception electrode 41 based on the transmission information subjected to the digital modulation. The modulated carrier waves are transmitted as the response signal from the power reception electrode 41 to the human body serving as a communication medium.

Figure 5:
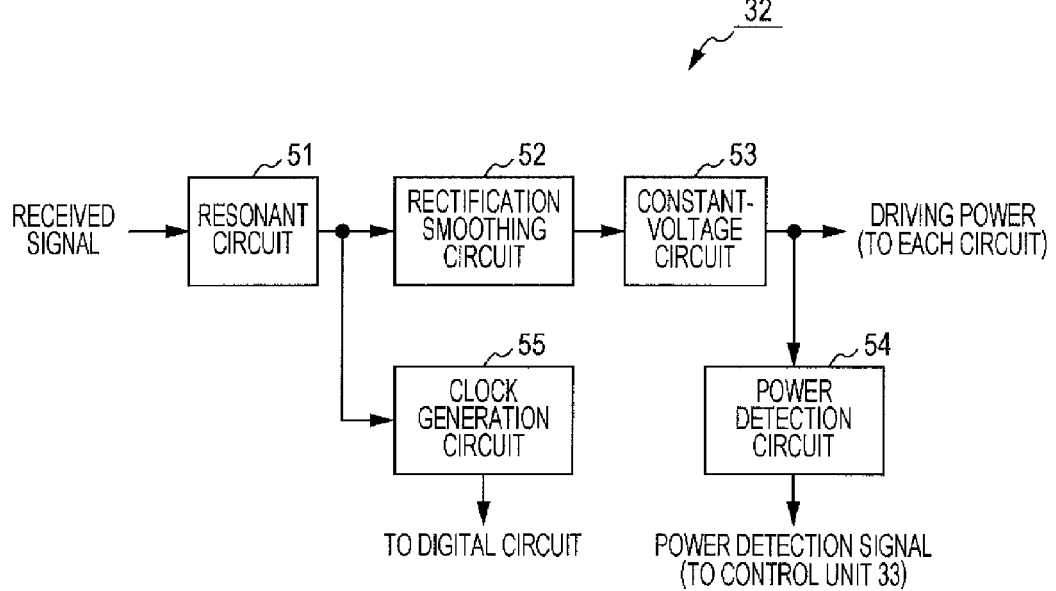
FIG. 5 is a diagram illustrating an example of the configuration of a reception unit of the responder shown in FIG. 3.

FIG. 5 is a diagram illustrating an example of the configuration of the power reception unit 32 (the power reception unit 42 of the responder 12 shown in FIG. 4) of the responder 12 shown in FIG. 3. The illustrated power reception unit 32 includes a resonant circuit 51, a rectification smoothing circuit 52, a constant-voltage circuit 53, a power detection circuit 54, and a clock generation circuit 55.

The resonant circuit 51 includes, for example, an LC circuit and is configured to resonate at a frequency unique for the responder 12.

The rectification smoothing circuit 52 rectifies and smoothes the output signal of the resonant circuit 51. As a rectification method, there are a half-wave rectification and a full-wave rectification. The output signal can be smoothed by lowering a ripple content of the rectified output signal.

The constant-voltage circuit 53 maintains the input voltage from the rectification smoothing circuit 52 so as to be constant. When the power detection circuit 54 detects that the output voltage of the constant-voltage circuit 53 reaches a voltage equal to or more than a predetermined voltage from a value smaller than a predetermined voltage, the power detection circuit 54 outputs the power detection signal to the control unit 33. For example, as the power detection signal, a pulse with a constant width is output when the power detection signal is detected. The predetermined voltage is a voltage that is sufficient to drive each circuit of the responder 12. The control unit 33 gives instructions to acquire the biological information and transmit the response signal in response to the power detection signal. The output of the constant-voltage circuit 53 becomes power used to drive each circuit.

The clock generation circuit 55 generates a necessary clock from the non-modulated carrier waves received by the power reception electrode 31 as a digital operation. For example, the clock can be generated by setting the average value of the non-modulated carrier waves as a threshold and digitalizing the signal. The generated clock is used in the operation of the digital circuit of the control unit 33 or the transmission unit 34.

It should be understood by those skilled in the art that various modifications, combinations, sub-combinations and alterations may occur depending on design requirements and other factors insofar as they are within the scope of the appended claims or the equivalents thereof.

What is claimed is:

1. A communication system comprising:
   an interrogator that:
      switches a carrier wave frequency of a non-modulated interrogation signal among a plurality of carrier wave frequencies for transmission of the non-modulated interrogation signal; and
      transmits the non-modulated interrogation signal in each of the plurality of carrier wave frequencies and receives a response signal in response to the transmitted non-modulated interrogation signal; and a plurality of responders each having a unique resonant frequency corresponding to one of the plurality of carrier wave frequencies, wherein each of the plurality of responders that is tuned to a corresponding switched carrier-wave frequency communicates the response signal to the interrogator in response to the transmitted non-modulated interrogation signal, wherein the interrogator performs switching of the carrier wave frequency based on a decision that information of the response signal is completely acquired from one of the plurality of responders, and wherein the plurality of responders comprise a clock generation circuit generating, from the non-modulated interrogation signal, a clock for a digital operation of the plurality of responders or another circuit, wherein the clock is generated by setting the average value of the non-modulated interrogation signal as a threshold and digitizing the non-modulated interrogation signal.

2. The communication system according to claim 1, wherein the interrogator transmits the non-modulated interrogation signal from a power feeding electrode in contact with a human body serving as a communication medium, and receives the response signal via the human body using the power feeding electrode, and wherein the plurality of responders each includes a sensor acquiring biological information from the human body, receives the non-modulated interrogation signal transmitted via the human body using a power reception electrode, and transmits the response signal in which the biological information acquired by the sensor is superimposed from the power reception electrode to the human body.

3. A communication apparatus comprising:
an oscillation unit switching an oscillation frequency among a plurality of oscillation frequencies in a predetermined sequence;
a transceiver transmitting a non-modulated interrogation signal with each of the plurality of oscillation frequencies to a communication medium and receiving a response signal in response to the transmitted non-modulated interrogation signal from the communication medium; and
a demodulation unit demodulating the received response signal, wherein the response signal is received from each of a plurality of responders tuned to one of the plurality of oscillation frequencies, wherein power is fed through the communication medium to one of the plurality of responders that is tuned to a currently switched oscillation frequency of the non-modulated interrogation signal to communicate the response signal to the communication medium,
wherein the oscillation unit performs switching of the oscillation frequency based on a decision that information of the response signal is completely acquired from one of the plurality of responders, and
wherein the plurality of responders comprise a clock generation circuit generating, from the non-modulated interrogation signal, a clock for a digital operation of the plurality of responders or another circuit, wherein the clock is generated by setting the average value of the non-modulated interrogation signal as a threshold and digitizing the non-modulated interrogation signal.

4. The communication apparatus according to claim 3, wherein the transceiver is configured by a power feeding electrode being in contact with a human body serving as the communication medium.

5. The communication apparatus according to claim 3, wherein the demodulation unit extracts information superimposed in the response signal.

6. The communication apparatus according to claim 3, further comprising a control unit operable to:
instruct the oscillation unit to perform switching of the oscillation frequency among the plurality of oscillation frequencies to acquire information from other of the plurality of responders.

7. A communication apparatus comprising:
a transceiver comprising a power reception electrode, the transceiver receiving a non-modulated interrogation signal via a communication medium, wherein the non-modulated interrogation signal comprises non-modulated carrier waves of a unique frequency;
a power reception unit resonating by the non-modulated interrogation signal with the unique frequency; and
a modulation unit configured to switch a state of a terminal of the power reception electrode to one of an open state or a ground state in response to the received non-modulated interrogation signal, wherein power is fed to the power reception electrode when the power reception unit is tuned to a currently switched frequency of the non-modulated interrogation signal to communicate a response signal to the communication medium,
wherein an interrogator, that transmits the non-modulated interrogation signal, switches from the currently switched frequency of the non-modulated interrogation signal to another frequency based on a decision that information of the response signal is completely acquired by the interrogator from the modulation unit, and
wherein the power reception unit comprises a clock generation circuit generating, from the non-modulated interrogation signal, a clock for a digital operation of the transceiver or another circuit, wherein the clock is generated by setting the average value of the non-modulated interrogation signal as a threshold and digitizing the non-modulated interrogation signal.

8. The communication apparatus according to claim 7, wherein the power reception electrode is in contact with a human body serving as the communication medium.

9. The communication apparatus according to claim 7, wherein the power reception unit resonates by the non-modulated interrogation signal with the unique frequency, generates constant-voltage power, and operates a transmission unit autonomously to transmit the response signal when the constant-voltage power has a reception voltage greater than a threshold voltage.

10. The communication apparatus according to claim 7, wherein the communication apparatus comprises a sensor function unit that acquires biological information from a human body.

11. The communication apparatus according to claim 7, wherein the transceiver transmits the response signal subjected to load modulation based on transmission information in response to the non-modulated interrogation signal.

* * * * *